US007514219B2

(12) United States Patent
Showe et al.

(10) Patent No.: US 7,514,219 B2
(45) Date of Patent: Apr. 7, 2009

(54) METHOD FOR DISTINGUISHING BETWEEN HEAD AND NECK SQUAMOUS CELL CARCINOMA AND LUNG SQUAMOUS CELL CARCINOMA

(75) Inventors: Louise C. Showe, Media, PA (US); Michael Nebozhyn, Yeadon, PA (US); Anil Vachani, Merion Station, PA (US); Steven M. Albelda, Bala Cynwyd, PA (US)

(73) Assignees: The Wistar Institute, Philadelphia, PA (US); Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/560,410

(22) Filed: Nov. 16, 2006

(65) Prior Publication Data
US 2007/0264644 A1 Nov. 15, 2007

Related U.S. Application Data

(60) Provisional application No. 60/737,228, filed on Nov. 16, 2005.

(51) Int. Cl.
*C12Q 1/68* (2006.01)
*C07H 21/02* (2006.01)
(52) U.S. Cl. .......................... 435/6; 536/23.1
(58) Field of Classification Search ................ 536/23.1; 435/6
See application file for complete search history.

(56) References Cited

OTHER PUBLICATIONS

Vachani et al (Clinical Cancer Research, May 2007, 13(10): 2905-2915).*
Tockman et al (Cancer Res., 1992, 52:2711s-2718s).*
Greenbaum et al. (Genome Biology, 2003, vol. 4, Issue 9, pp. 117.1-117.8).*
Lee et al (Mechanisms of Development, Mar. 2001, 293-297).*
Singhal et al (Journal of the American College of Surgeons, Sep. 2004, 199(3s): s66-s67).*
Belbin et al., "Molecular Classification of Head and Neck Squamous Cell Carcinoma Using cDNA Microarrays", Cancer Research 2003 62:1184-1190.
Bhattacharjee et al., "Classification of human lung carcinomas by mRNA expression profiling reveals distinct adenocarcinoma subclasses", Proc. Natl. Acad. Sci. USA 2001 98(24):13790-13795.
Borczuk et al., "Molecular Signatures in Biopsy Specimens of Lung Cancer", Am J Respir Crit Care Med 2004 170:167-174.
Borczuk et al., "Non-Small-Cell Lung Cancer Molecular Signatures Recapitulate Lung Developmental Pathways", American Journal of Pathology 2003 163(5):1949-1960.
Geurts et al., "Pulmonary Squamous Cell Carcinoma following Head and Neck Squamous Cell Carcinoma:Metastasis or Secondary Primary?", Clin Cancer Res 2005 11(18):6608-6614.
Ginos et al., "Identification of a Gene Expression Signature Associated with Recurrent Disease in Squamous Cell Carcinoma of the Head and Neck", Cancer Research 2004 64:55-63.
Giordano et al., "Organ-Specific Molecular Classification of Primary Lung, Colon, and Ovarian Adenocarcinomas Using Gene Expression Profiles", Am J Pathol 2001 159:1231-1238.
Leong et al., "Distinguishing Second Primary Tumors From Lung Metastases in Patients With Head and Neck Squamous Cell Carcinoma", J Natl. Cancer Inst 1998 90:972-977.
Melloni et al., "Prognostic significance of cancer-testis gene expression in resected non-small cell lung cancer patients", Oncology Reports 2004 12:145-151.
Nishizuka et al., "Diagnostic Markers That Distinguish Colon and Ovarian Adenocarcinomas:Identification by Genomic, Proteomic, and Tissue Array Profiling", Cancer Research 2003 63:5243-5250.
Ramaswamy et al., "Multiclass cancer diagnosis using tumor gene expression signature", Proc. Natl. Acad. Sci. USA 2001 98(26):15149-15154.
Talbot et al., "Gene Expression Profiling Allows Distinction between Primary and Metastatic Squamous Cell Carcinomas in the Lung", Cancer Res 2005 65(8):3063-3071.

* cited by examiner

*Primary Examiner*—Sean E Aeder
(74) *Attorney, Agent, or Firm*—Licata & Tyrrell P.C.

(57) ABSTRACT

The present invention is a method distinguishing between head and neck squamous cell carcinoma and lung squamous cell carcinoma. In particular, a 10-gene classifier has been identified which can be used to distinguish between primary squamous cell carcinoma of the lung and metastatic head and neck squamous cell carcinoma. These genes include CXCL13, COL6A2, SFTPB, KRT14, TSPYL5, TMP3, KLK10, MMP1, GAS1, and MYH2. A panel of one or more of these genes, or proteins encoded thereby, can be used for early diagnosis and selection of an appropriate therapeutic treatment.

4 Claims, No Drawings

METHOD FOR DISTINGUISHING BETWEEN HEAD AND NECK SQUAMOUS CELL CARCINOMA AND LUNG SQUAMOUS CELL CARCINOMA

INTRODUCTION

This application claims benefit of U.S. Provisional Patent Application Ser. No. 60/737,228, filed Nov. 16, 2005, the content of which is incorporated herein by reference in its entirety.

This invention was made in the course of research sponsored by the National Cancer Institute (Grant Nos. T32 CA09171, K12 CA076931 and caBIG Contract 79522CBS10) and the National Science Foundation (Grant No. RCN 0090286). The U.S. government may have certain rights in this Invention.

BACKGROUND OF THE INVENTION

Patients with head and neck squamous cell carcinoma (HNSCC) are at high risk for the development of metastatic carcinoma in the lung. Studies suggest that 5-15% of patients with HNSCC develop lung metastases (Ferlito, et al. (2001) *ORL J. Otorhinolaryngol. Relat. Spec.* 63:202-7). However, because patients with HNSCC are often heavy tobacco users, they are also at risk for second primary cancers, with squamous cell carcinoma of the lung (LSCC) being the most common (Jones, et al. (1995) *Cancer* 75:1343-53).

In some cases, the distinction between a lung metastasis and a second primary lung carcinoma can be distinguished on clinical grounds. The presence of multiple pulmonary nodules is usually considered evidence of metastatic disease. However, in subjects who present with a solitary lung nodule, the distinction between metastasis and primary carcinoma can be more problematic. Usually, patients with HNSCC who are found to have solitary pulmonary lesions undergo surgery or needle biopsy with pathologic evaluation. If the lung lesion is also of squamous cell histology, the distinction between metastasis and primary LSCC is extremely difficult. Currently this distinction is made by comparison of histological grade or by the presence of other premalignant changes in the respiratory epithelium; however, the accuracy of this approach is unclear.

Making the correct diagnosis has practical importance for choice of therapy. Although patients with either a primary LSCC or a solitary HNSCC metastases may be eligible for surgical resection, the surgical procedure (wedge resection versus lobectomy) and the use of adjuvant therapy is usually different in these situations. Additionally, patients with early stage LSCC have a significantly better prognosis than patients with metastatic HNSCC.

Recent gene expression studies have demonstrated the potential to classify the origin of human carcinomas cell lines (Nishizuka, et al. (2003) *Cancer Res.* 63:5243-50) and human tumors (Giordano, et al. (2001) *Am. J. Pathol.* 159:1231-8; Ramaswamy, et al. (2001) *Proc. Natl. Acad. Sci. USA* 98:15149-54). Although a number of studies have examined gene profiles in head and neck squamous cell carcinomas (Ginos, et al. (2004) *Cancer Res.* 64:55-63; Belbin, et al. (2002) *Cancer Res.* 62:1184-90) and lung squamous cell cancers (Borczuk, et al. (2003) *Am. J. Pathol.* 163:1949-60) with their tissues of origin, the patterns in these two types of tumors have only been compared in one previous study (Talbot, et al. (2005) *Cancer Res.* 65:3063-71). In this study, gene expression profiling was used to compare 21 lung cancer and 31 tongue cancer samples, wherein a distinction between HNSCC and LSCC tumors was achieved using hierarchical clustering with gene sets of 100-500 genes. The accuracy of these predictions decreased when the number of genes was reduced below 100.

Moreover, the use of genetic abnormalities has been suggested to distinguish between a primary lung tumor and pulmonary metastases. Paired tumors from 16 patients with HNSCC and a solitary lung nodule were compared for loss of heterozygosity on chromosomal arms 3p and 9p (Leong, et al. (1998) *J. Natl. Cancer Inst.* 90:972-7). The use of loss of heterozygosity distinguished 13 of the 16 cases as primary lung cancer or metastasis based on discordant versus concordant allelic patterns between the index tumor and the lung lesion. A separate study using loss of heterozygosity suggests that many squamous lung lesions in patients with HNSCC, that are currently classified as metastases based on clinical criteria, may in fact be primary lung cancers (Geurts, et al. (2005) *Clin. Cancer Res.* 11:6608-14). Although loss of heterozygosity is potentially useful, this technique is time consuming, not widely available, not completely accurate, and most importantly, requires appropriate tissue from both the primary and the lung lesion.

Needed in the art is a reliable method for distinguishing between primary and metastatic squamous cell carcinoma of the lung using a small number of differentially expressed genes. The present invention meets this long-felt need in the art.

SUMMARY OF THE INVENTION

The present invention is a reference profile for distinguishing between head and neck squamous cell carcinoma and lung squamous cell carcinoma. The reference profile is an expression pattern for CXCL13, COL6A2, SFTPB, KRT14, TSPYL5, TMP3, KLK10, MMP1, GAS1, or MYH2, or a combination thereof.

The present invention is also a method for distinguishing between head and neck squamous cell carcinoma and lung squamous cell carcinoma. The method of the present invention involves determining a test profile for CXCL13, COL6A2, SFTPB, KRT14, TSPYL5, TMP3, KLK10, MMP1, GAS1, or MYH2, or a combination thereof, of a sample from a patient having or at risk of having a head and neck squamous cell carcinoma or lung squamous cell carcinoma and comparing the test profile with the instant reference profile or a normal control profile, wherein the compared profiles distinguish between head and neck squamous cell carcinoma and lung squamous cell carcinoma.

In particular embodiments of the present invention, the lung squamous cell carcinoma is a primary lung squamous cell carcinoma and the head and neck squamous cell carcinoma is metastatic.

DETAILED DESCRIPTION OF THE INVENTION

A panel of 10 differentially expressed genes have now been identified for distinguishing primary LSCC from pulmonary metastases of HNSCC. Gene expression patterns of RNA derived from 28 patients with HNSCC or LSCC from a single center were analyzed using penalized discriminant analysis (PDA). The panel of 10 genes (CXCL13, COL6A2, SFTPB, KRT14, TSPYL5, TMP3, KLK10, MMP1, GAS1, and MYH2) accurately distinguished these two tumor types and was validated on previously published data for 122 subjects (72 HNSCC, 50 LSCC) derived from 45 independent Affymetrix® datasets. An average accuracy of 96% was demonstrated. The 10-gene classifier was applied to gene expression data from 12 lung lesions from patients with prior HNSCC to determine whether their sites of origin could be correctly identified. The results indicated that PDA using these 10 genes is highly accurate in determining the origin of squamous cell carcinomas in the lungs of patients with previous head and neck malignancies. Accordingly, the panel of 10 genes disclosed herein is useful for distinguishing between primary and metastatic squamous cell carcinoma of the lung to facilitate the selection of an appropriate therapy for treatment.

To establish a set of genes which could distinguish between primary LSCC and pulmonary metastases, twenty-eight patients with surgical resection of their primary HNSCC or LSCC were evaluated. The clinical characteristics of these patients are presented in Table 1. Clinical data on all 28 subjects was collected via retrospective chart reviews and in certain cases by interview. In general, the two groups of patients were similar in age, gender, and racial distribution. None of the LSCC patients had a previous history of HNSCC cancer and none developed evidence of HNSCC during follow-up. Thus, all ten LSCC patients were judged to have true primary squamous cell carcinoma of the lung.

TABLE 1

| VARIABLE | HNSCC (n = 18) | LSCC (n = 10) |
| --- | --- | --- |
| Age, mean | 61 | 62 |
| Gender (%) | | |
| Male | 78 | 80 |
| Female | 22 | 20 |
| Race (%) | | |
| White | 83 | 90 |
| Black | 11 | 10 |
| Other | 6 | 0 |
| Pathologic T Stage (%) | | |
| T1 | 11 | 30 |
| T2 | 28 | 30 |
| T3 | 17 | 10 |
| T4 | 44 | 30 |
| Pathologic N Stage (%) | | |
| N0 | 39 | 80 |
| N1 | 11 | 20 |
| N2 | 50 | 0 |
| Histological Grade (%) | | |
| 1 | 5 | 0 |
| 2 | 56 | 70 |
| 3 | 39 | 30 |
| Tumor Site (%) | | |
| FOM/Buccal/Tonsil | 22 | NA |
| Gingiva | 6 | NA |
| Larynx | 0 | NA |
| Mandible | 11 | NA |
| Tongue | 61 | NA |

One cohort (18 HNSCC, 10 LSCC) from the University of Pennsylvania was analyzed with a Student's t-test. Out of 9530 probe sets common between Affymetrix® GeneChip® U95Av2 and GeneChip® U133A, 1879 probe sets had expression values with significant differences ($p<0.01$), with 820 and 1059 probe sets being up- and down-regulated in HNSCC, respectively. The conservative estimate for the expected number of false-positives expected in the context of multiple testing, would be $0.01 \times 9530 = 95$, thus leading to an expected false discovery rate of 5% (95/1879). Using a cutoff of p-value<0.01 and three-fold cut-off for the absolute value of the mean gene expression ratio, a total of 101 probe sets (representing 100 unique genes) were found to be significantly different between the two groups of samples. Of these 101 probe sets, 81 and 20 were up- and down-regulated respectively, in HNSCC. In hierarchical clustering analysis, one LSCC case was found to be clustered within the HNSCC group, rather than with the other 9 lung cancer samples.

The 28 patient samples were subsequently used in a training set using penalized discriminant analysis (PDA) with recursive feature elimination (RFE) to identify genes with the highest power to correctly distinguish patients with LSCC from those with HNSCC. It has been observed that genes selected by PDA perform better as classifiers than genes selected by t-test when applied to a new set of validation samples (Kari, et al. (2003) J. Exp. Med. 197:1477-88). The PDA program was trained on the 28 patients (10 LSCC, 18 HNSCC; Table 1) using the 9530 probe sets representing the overlap between the GeneChip® U95Av2 and GeneChip® U133A arrays. During the process of RFE by PDA, each probe set was assigned a gene rank that was a measure of the order in which a given probe set was eliminated in the course of RFE. The lower the rank number of a probe set, the more important the contribution to the discriminant score. The discriminant score assigned to each sample was a measure of how well that sample was classified by the selected genes. Based upon hierarchical clustering using the top 100 probe sets identified by PDA/RFE, all samples were correctly separated into the two different phenotypic groups. The 100 most significantly different probe sets between the two patient groups are listed in Table 2.

Some of the most useful discriminating genes were the lung surfactant genes, which were higher in the LSCC. Another major gene family with increased expression in lung cancers was the GAGE (G antigen) genes. GAGE proteins are a large group of cancer/testis antigens consisting of GAGE-1 through GAGE-8 (Emens & Jaffee (2002) Cancer Biol. Ther. 1:388-90). Although the function of most of the cancer/testes antigens is not known, GAGE proteins have been implicated in inhibition of apoptosis and chemotherapy resistance (Cilensek, et al. (2002) Cancer Biol. Ther. 1:380-7; Duan, et al. (2003) Clin. Cancer Res. 9:2778-85). GAGE protein expression is present in approximately 40% of lung cancers and is associated with poor prognosis (Melloni, et al. (2004) Oncol. Rep. 12:145-51). Detrimental effects of GAGE expression on survival has also been shown in esophageal and brain tumors (Cheung, et al. (2000) Med. Pediatr. Oncol. 35:632-4; Zambon, et al. (2001) Cancer 91:1882-8). Unexpectedly, GAGE gene expression was upregulated in only a subset of the LSCC (and no HNSCC).

Of particular interest was the difference in expression of specific cytokeratin genes in these two types of tumors. All eukaryotic cells contain a cytoskeleton composed of three distinct filamentous structures: microfilaments, intermediate filaments (IF), and microtubules (Barak, et al. (2004) Clin. Biochem. 37:529-40). The intermediate filament protein family includes several hundred different members that are divided into several groups. Cytokeratins constitute type I and type II intermediate filaments and are subdivided based on isoelectric point (CK 1-9 are acidic; CK 10-20 are basic). Stratified squamous epithelia express mostly CKs 1-6, and 9-17, while CKs 7, 8, and 18-20 are identified in simple epithelia (Barak, et al. (2004) supra). During malignant transformation of normal cells, the cytokeratin patterns are usually maintained.

The pattern of gene expression differences identified in the present expression profiling demonstrated a stratified squamous epithelial pattern in the HNSCC tumors with higher expression of CK 1 and 14 (up-regulated 3.6-and 62-fold, respectively) and lower expression of CK18 and 19 (down-regulated 3.9- and 10-fold, respectively). Although both upper airway epithelium and bronchial epithelium are composed of stratified squamous cells, HNSCC tumors appear to be more likely to exhibit a stratified squamous pattern given their location in the upper aerodigestive tract.

Many genes in the collagen family were also up-regulated in head and neck tumors when compared with squamous cell lung cancer. Five collagen-related genes (COL6A2, COL1A2, COL10A1, COL3A1, COL6A3) were found in the top 100 genes selected by PDA and had expression ratios ranging from +1.8 to +4.0. In the tumor microenvironment, collagens are a major component of the extracellular matrix, which is primarily secreted by stromal cells and inflammatory cells (Bhowmick & Moses (2005) *Curr. Opin. Genet. Dev.* 15:97-101). Thus, the higher expression of collagen in the head and neck tumors may reflect a higher proportion of stromal elements as compared to the lung cancer samples. There is data, however, that suggests that certain collagen genes are expressed in the tumor cells themselves. For example, ovarian cancer cells have been shown to highly express several ECM proteins including Collagen VI and this was associated with resistance to cisplatin in vitro (Sherman-Baust, et al. (2003) *Cancer Cell* 3:377-86).

The high expression of collagens in the head and neck tumors was mirrored by higher levels of three matrix metalloproteinases, MMP1, MMP3, MMP10, which were increased by 12.4-, 8.2-, and 2.6-fold, respectively, when compared to the lung cancers. MMP-1, or collagenase-1, is expressed in a wide variety of cancers and in most cases is associated with increased invasion and poorer survival (Brinckerhoff, et al. (2000) *Clin. Cancer Res.* 6:4823-30). MMP-3, which is a secreted by fibroblasts, can activate tumor-derived MMP-1 and other collagenases leading to increased collagen degradation and tumor invasion (Brinckerhoff, et al. (2000) supra) . In head and neck tumors, high levels of MMP-1 and MMP-3 are associated with greater tumor invasiveness and incidence of lymph node metastases (Kurahara, et al. (1999) *Head Neck* 21:627-38). The higher levels of MMP gene expression in the instant study may have been due to higher proportion of HNSCC tumors with lymph nodes metastases when compared with the LSCC tumors (61% versus 20%).

TABLE 2

| Gene Symbol | Gene Title | UniGene ID | PDA Rank | Mean Ratio |
|---|---|---|---|---|
| CXCL13 | chemokine (C-X-C motif) ligand 13 | Hs.100431 | 1 | +2.3 |
| COL6A2 | collagen, type VI, alpha 2 | Hs.420269 | 2 | +4.0 |
| SFTPB | surfactant, pulmonary-associated protein B | Hs.512690 | 3 | −35.3 |
| KRT14 | keratin 14 | Hs.355214 | 4 | +62.3 |
| TSPYL5 | TSPY-like 5 | Hs.173094 | 5 | −4.6 |
| TPM3 | tropomyosin 3 | Hs.146070 | 6 | +2.9 |
| KLK10 | kallikrein 10 | Hs.275464 | 7 | +5.0 |
| MMP1 | matrix metalloproteinase 1 | Hs.83169 | 8 | +12.4 |
| GAS1 | growth arrest-specific 1 | Hs.65029 | 9 | +3.1 |
| MYH2 | myosin, heavy polypeptide 2, skeletal muscle, adult | Hs.513941 | 10 | +5.8 |
| TRIM22 | tripartite motif-containing 22 | Hs.501778 | 11 | +5.3 |
| SERPINB2 | serine (or cysteine) proteinase inhibitor, clade B (ovalbumin), member 2 | Hs.514913 | 12 | +5.7 |
| HBB | hemoglobin, beta | Hs.523443 | 13 | −3.4 |
| SCGB1A1 | secretoglobin, family 1A, member 1 (uteroglobin) | Hs.523732 | 14 | −8.8 |
| HLA-DPA1 | major histocompatibility complex, class II, DP alpha 1 | Hs.347270 | 15 | +2.2 |
| MUC5B | mucin 5, subtype B, tracheobronchial | Hs.523395 | 16 | −1.8 |
| IGFBP3 | insulin-like growth factor binding protein 3 | Hs.450230 | 17 | −1.8 |
| LGALS7 | lectin, galactoside-binding, soluble, 7 (galectin 7) | Hs.99923 | 18 | +6.4 |
| KRT19 | keratin 19 | Hs.514167 | 19 | −10.8 |
| MMP3 | matrix metalloproteinase 3 | Hs.375129 | 20 | +8.2 |
| LEPR | leptin receptor | Hs.23581 | 21 | +1.7 |
| PTGIS | prostaglandin I2 (prostacyclin) synthase | Hs.302085 | 22 | −1.8 |
| LDB3 | LIM domain binding 3 | Hs.49998 | 23 | +1.9 |
| NEFL | neurofilament, light polypeptide 68 kDa | Hs.521461 | 24 | +1.8 |
| TDO2 | tryptophan 2,3-dioxygenase | Hs.183671 | 25 | +1.6 |
| SERPINB1 | serine (or cysteine) proteinase inhibitor, clade B (ovalbumin), member 1 | Hs.381167 | 26 | +3.2 |
| HBB | hemoglobin, beta | Hs.523443 | 27 | −4.0 |
| COL1A2 | collagen, type I, alpha 2 | Hs.489142 | 28 | +3.6 |
| SFTPD | surfactant, pulmonary-associated protein D | Hs.253495 | 29 | −5.3 |
| GAGE1 | G antigen 1 | Hs.278606 | 30 | −4.9 |
| COL10A1 | collagen, type X, alpha 1(Schmid metaphyseal chondrodysplasia) | Hs.520339 | 31 | +1.8 |

TABLE 2-continued

| Gene Symbol | Gene Title | UniGene ID | PDA Rank | Mean Ratio |
|---|---|---|---|---|
| APOC1 | apolipoprotein C-I | Hs.110675 | 32 | −2.0 |
| NTS | neurotensin | Hs.80962 | 33 | −6.6 |
| CAV2 | caveolin 2 | Hs.212332 | 34 | +3.9 |
| SERPINB3 | serine (or cysteine) proteinase inhibitor, clade B (ovalbumin), member 3 | Hs.227948 | 35 | +3.5 |
| PI3 | protease inhibitor 3, skin-derived (SKALP) | Hs.112341 | 36 | +9.3 |
| ANK3 | ankyrin 3, node of Ranvier (ankyrin G) | Hs.499725 | 37 | +1.8 |
| CXADR | coxsackie virus and adenovirus receptor | Hs.473417 | 38 | −1.5 |
| LYZ | lysozyme (renal amyloidosis) | Hs.524579 | 39 | +2.6 |
| YWHAZ | tyrosine 3-monooxygenase/tryptophan 5-monooxygenase activation protein, zeta polypeptide | Hs.492407 | 40 | +3.2 |
| SERPINA1 | serine (or cysteine) proteinase inhibitor, clade A (alpha-1 antiproteinase, antitrypsin), member 1 | Hs.525557 | 41 | −3.2 |
| CXCL12 | chemokine (C-X-C motif) ligand 12 | Hs.522891 | 42 | +1.8 |
| COL3A1 | collagen, type III, alpha 1 | Hs.443625 | 43 | +2.8 |
| GAGE5 | G antigen 5 | Hs.278606 | 44 | −4.3 |
| FN1 | fibronectin 1 | Hs.203717 | 45 | +2.1 |
| GAGE2 | G antigen 2 | Hs.278606 | 46 | −4.3 |
| TncRNA | Trophoblast-derived noncoding RNA | Hs.523789 | 47 | +3.2 |
| ANXA8 | annexin A8 | Hs.463110 | 48 | +2.8 |
| COL6A3 | collagen, type VI, alpha 3 | Hs.233240 | 49 | +2.7 |
| SFTPC | surfactant, pulmonary-associated protein C | Hs.1074 | 50 | −6.4 |
| THBS4 | thrombospondin 4 | Hs.211426 | 51 | +2.5 |
| IL1R2 | interleukin 1 receptor, type II | Hs.25333 | 52 | +3.1 |
| ACTA1 | actin, alpha 1, skeletal muscle | Hs.1288 | 53 | +9.9 |
| KRT1 | keratin 1 (epidermolytic hyperkeratosis) | Hs.80828 | 54 | +3.6 |
| PTHLH | parathyroid hormone-like hormone | Hs.89626 | 55 | +3.1 |
| TKTL1 | transketolase-like 1 | Hs.102866 | 56 | −1.5 |
| IFI44 | interferon-induced protein 44 | Hs.82316 | 57 | +6.7 |
| CAV1 | caveolin 1, caveolae protein, 22 kDa | Hs.74034 | 58 | +3.8 |
| CTGF | connective tissue growth factor | Hs.410037 | 59 | +2.0 |
| CDH1 | cadherin 1, type 1, E-cadherin (epithelial) | Hs.461086 | 60 | +1.8 |
| GAGE2 | G antigen 2 | Hs.278606 | 61 | −3.9 |
| ME1 | malic enzyme 1, NADP(+)-dependent, cytosolic | Hs.21160 | 62 | +1.7 |
| FHL1 | four and a half LIM domains 1 | Hs.435369 | 63 | +2.8 |
| MMP10 | matrix metalloproteinase 10 | Hs.2258 | 64 | +2.6 |
| PTPRZ1 | protein tyrosine phosphatase, receptor-type, Z polypeptide 1 | Hs.489824 | 65 | +3.2 |
| ABCA3 | ATP-binding cassette, sub-family A (ABC1), member 3 | Hs.26630 | 66 | −4.0 |
| RARRES2 | retinoic acid receptor responder (tazarotene induced) 2 | Hs.521286 | 67 | −1.7 |
| POSTN | periostin, osteoblast specific factor | Hs.136348 | 68 | +3.6 |
| GCLM | glutamate-cysteine ligase, modifier subunit | Hs.315562 | 69 | +1.9 |
| DSG3 | desmoglein 3 (pemphigus vulgaris antigen) | Hs.1925 | 70 | +8.1 |
| CSRP3 | cysteine and glycine-rich protein 3 (cardiac LIM protein) | Hs.83577 | 71 | +5.4 |
| NID | nidogen (enactin) | Hs.356624 | 72 | +2.4 |
| PHLDA2 | pleckstrin homology-like domain, family A, member 2 | Hs.154036 | 73 | +2.1 |
| TNC | tenascin C (hexabrachion) | Hs.143250 | 74 | +3.7 |
| KLK13 | kallikrein 13 | Hs.165296 | 75 | +2.7 |
| IGFBP2 | insulin-like growth factor binding protein 2, 36 kDa | Hs.438102 | 76 | −2.7 |
| PLEC1 | plectin 1, intermediate filament binding protein 500 kDa | Hs.434248 | 77 | +1.4 |
| SFRP4 | secreted frizzled-related protein 4 | Hs.105700 | 78 | +1.5 |
| CMKOR1 | chemokine orphan receptor 1 | Hs.471751 | 79 | +1.6 |
| C4BPA | complement component 4 binding protein, alpha | Hs.1012 | 80 | −3.6 |

TABLE 2-continued

| Gene Symbol | Gene Title | UniGene ID | PDA Rank | Mean Ratio |
|---|---|---|---|---|
| SFRP1 | secreted frizzled-related protein 1 | Hs.213424 | 81 | +2.3 |
| CYR61 | cysteine-rich, angiogenic inducer, 61 | Hs.8867 | 82 | +1.7 |
| C14orf109 | chromosome 14 open reading frame 109 | Hs.275352 | 83 | +1.8 |
| PYGL | phosphorylase, glycogen; liver (Hers disease, glycogen storage disease type VI) | Hs.282417 | 84 | +3.6 |
| FGFBP1 | fibroblast growth factor binding protein 1 | Hs.1690 | 85 | +3.6 |
| TPM2 | tropomyosin 2 (beta) | Hs.300772 | 86 | +4.5 |
| WNT5A | wingless-type MMTV integration site family, member 5A | Hs.152213 | 87 | +3.5 |
| SERPINB4 | serine (or cysteine) proteinase inhibitor, clade B (ovalbumin), member 4 | Hs.123035 | 88 | +3.3 |
| GAGE4 | G antigen 4 | Hs.278606 | 89 | −3.8 |
| KRT18 | keratin 18 | Hs.406013 | 90 | −3.9 |
| EDNRA | endothelin receptor type A | Hs.183713 | 91 | +1.6 |
| RGS1 | Regulator of G-protein signalling 1 | Hs.75256 | 92 | +2.7 |
| CTSH | cathepsin H | Hs.148641 | 93 | −1.9 |
| WSB1 | WD repeat and SOCS box-containing 1 | Hs.446017 | 94 | +2.1 |
| LUM | lumican | Hs.406475 | 95 | +3.1 |
| S100A7 | S100 calcium binding protein A7 (psoriasin 1) | Hs.112408 | 96 | +53.6 |
| CXCL6 | chemokine (C-X-C motif) ligand 6 (granulocyte chemotactic protein 2) | Hs.164021 | 97 | −1.6 |
| MYL1 | myosin, light polypeptide 1, alkali; skeletal, fast | Hs.187338 | 98 | +5.7 |
| CCND2 | cyclin D2 | Hs.376071 | 99 | +1.8 |
| SQLE | squalene epoxidase | Hs.71465 | 100 | +2.1 |

PDA rank: the order in which the given gene was eliminated during the course of recursive feature elimination.
Mean ratio: ratio of mean gene expression ratio in one group versus the other. A positive ratio corresponds to higher expression in HNSCC and a negative ratio corresponds to higher expression in LSCC.

To test the accuracy of the differentially expressed genes identified by PDA, the genes were analyzed on completely independent sets of samples obtained from Memorial-Sloan Kettering Cancer Center (18 LSCC, 31 HNSCC), the Dana-Farber Cancer Institute (21 LSCC), University of Minnesota (41 HNSCC) and Columbia University (11 LSCC). An evaluation of systematic biases in the data sets that might be due to source (where the samples were isolated and processed) or to the array platform used (U95Av2 or U133A arrays) was conducted. When the data from the 28 patient sample set from the University of Pennsylvania was tested by hierarchical clustering using the 9,530 overlapping genes, a perfect separation by phenotype for these different tumor types was achieved. When applying unsupervised hierarchical clustering using the 9,530 common genes to all 150 samples (i.e., Memorial-Sloan Kettering Cancer Center, the Dana-Farber Cancer Institute, University of Minnesota, Columbia University and University of Pennsylvania), the samples did not cluster by tumor type. Rather, the samples clustered first according to the Affymetrix® chip (U95Av2 versus U133A) used for the study and then according to the source of the data (i.e., the five institutions). To minimize the artificial variability due to different institutions and chip versions, Distance Weighted Discrimination (DWD) was applied. DWD has been reported to be successful in correcting for data set biases due to platform and/or data source (Benito, et al. (2004) *Bioinformatics* 20:105-14). DWD is designed to correct the systematic bias in one dataset at a time, and in the instant case of several datasets with multiple biases due to the data source and the chip used for hybridization. The DWD correction for the instant data set was carried out in the following order but the results were essentially the same regardless of the order in which the data were merged. First, the 41 HNSCC samples in the University of Minnesota dataset were merged with the 18 HNSCC samples from the University of Pennsylvania (both on GENECHIP® U133A). The 11 LSCC from Columbia University were then merged with the 10 University of Pennsylvania LSCC samples (GENECHIP® U95Av2 and GENECHIP® U133A, respectively). The 21 Dana-Farber Cancer Institute LSCC were also merged with the 10 LSCC University of Pennsylvania samples. Finally, the two data sets with values for both HNSCC and LSCC, those from Memorial-Sloan Kettering Cancer Center and the University of Pennsylvania, were merged. For every correction, the datasets undergoing adjustment were centered to the corresponding University of Pennsylvania dataset. Hierarchical clustering performed after DWD correction provided all 150 samples clustered according to tumor type, with no subclustering by chip type or location observed.

The discriminant model using the genes identified by PDA with RFE on the University of Pennsylvania training set was then applied to classify 72 HNSCC and 50 LSCC samples in the DWD-adjusted validation cohort. The observed accuracy of classification as a function of the total number of genes retained in the discriminant model was determined. Values were obtained for classifiers ranging from 1-100 genes. There was little change in accuracy between 100 and 10 genes. Using a 10-gene classifier, the measurements of average accuracy, the sensitivity, and the specificity were each calculated to be 96%. Therefore, 10 genes were sufficient to robustly discriminate the HNSCC samples from LSCC samples in the validation set.

In applying the 10-gene classifier, each sample in the validation set was given a discriminant score that was a measure of how well it was classified. Positive and negative scores indicated that the sample was classified as HNSCC or LCSCC, respectively. Of the 122 total samples, only 5 samples were misclassified, 3 LSCC and 2 HNSCC samples. Two of the misclassified LSCC were borderline cases. The 10 genes used for the classification included: chemokine ligand 13 (CXCL13); collagen, type VI, alpha 2 (COL6A2); surfactant protein B (SFTPB); keratin 14 (KRT14); TSPY-like 5 (TSPYL5); tropomyosin 3 (TMP3); kallikrein 10 (KLK10); matrix metalloproteinase 1 (MMP1); growth arrest-specific 1(GAS1); and myosin, heavy polypeptide 2, skeletal muscle, adult (MYH2).

The gene expression values determined for the University of Pennsylvania array dataset were confirmed using two methods. First, the gene expression ratios (HNSCC/LSCC) of 19 genes were compared to the ratios obtained from the same genes in the Memorial-Sloan Kettering Cancer Center datasets. Second, quantitative real-time PCR (QRT-PCR) on samples derived from a new group of seven HNSCC subjects and five LSCC subjected which had not been previously analyzed on microarrays was used to confirm gene expression ratios determined by microarrays on these 19 genes. Only on of the 19 genes had an expression ratio that did not agree among the three data datasets, COL6A2 had higher expression in HNSCC compared to LSCC in the University of Pennsylvania array study and by QRT-PCR, whereas its expression in HNSCC was slightly lower in the Memorial-Sloan Kettering Cancer Center dataset.

Using QRT-PCR data on seven genes, gene expression ratios (nine HNSCC, seven LSCC) were calculated using an established method (Gordon, et al. (2002) *Cancer Res.* 62:4963-7). Briefly, the expression values for five genes expressed at significantly higher levels in HNSCC were divided by the gene expression values of two genes expressed at high levels in LSCC, but much lower levels in HNSCC. The diagnostic accuracies of the nine best performing ratios were determined, wherein all nine of these ratios accurately separated these two tumor types with differences approaching 1,000-fold in some cases.

Having identified a 10-gene classifier with high accuracy for distinguishing between primary lung carcinoma from metastatic head and neck carcinomas, it was then determined whether the algorithm would be similarly accurate in the classification of a set of 12 squamous cell lung tumors resected from 12 patients previously treated for primary HNSCC. Classification of these samples using a 500-gene classifier that discriminated HNSCC from LSCC has been described (Talbot, et al. (2005) supra). Although these samples could not definitively be distinguished as lung primaries or lung metastases, based on pathologic or clinical criteria most of the lesions were suspected to be of lung origin (Talbot, et al. (2005) supra). When the instant 10-gene classifier identified by PDA with RFE was tested on these 12 samples, the majority (U01 through U11) had strong negative classification scores, indicating that they were primary lung carcinomas as was suspected (Talbot, et al. (2005) supra). Sample U12, which was clinically thought to be a lung metastasis based on the development of an additional pancreatic metastasis in the patient, was classified using that 10-gene classifier as HNSCC, supporting the clinical impression. Sample U13, which was a pancreatic metastasis from the same patient as U12, was also classified using the 10-gene classifier as HNSCC, although not as robustly, indicating that it retains the HNSCC gene signature.

To determine whether the analysis conducted herein was contaminated that normal lung tissue, immmunohistochemical studies were conducted on selected tissue samples. The initial gene expression analysis demonstrated highly significant differences in the expression of surfactant protein genes between HNSCC and LSCC tissues. Surfactant proteins B, C, and D were much more highly expressed in LSCC compared with HNSCC, with fold changes of 35.3, 6.4, and 5.3, respectively. To demonstrate that the high surfactant gene expression was not due to contamination from adjacent normal lung tissue, the distribution of one of these surfactant proteins was examined using immunohistochemistry with an antibody against surfactant protein-C (SP-C) that worked well in paraffin sections on four LSCC samples. In all cases, high or moderate cytoplasmic staining was clearly seen from within the tumor cells themselves, thus demonstrating that the high level of surfactant gene expression in lung squamous carcinomas was primarily due to true tumor cell expression and not normal lung tissue contamination.

One advantage of the discriminant model disclosed herein over the traditional hierarchical clustering/t-test approach is the accuracy that was achieved using a small number of genes. The instant 10-gene classifier correctly classified 96% of the 49 samples from an established set of samples (Talbot, et al. (2005) supra) and accurately evaluated external datasets from several other institutions. While the data disclosed herein were derived from primary LSCC and HNSCC samples, it is contemplated that the predictive approach of the present invention will be able to determine the origin of lung nodules in patients with previous HNSCC.

Accordingly, the present invention is a reference profile for distinguishing between head and neck squamous cell carcinoma and lung squamous cell carcinoma. The reference profile of the invention is composed of an expression pattern for CXCL13, COL6A2, SFTPB, KRT14, TSPYL5, TMP3, KLK10, MMP1, GAS1, or MYH2 (also referred to herein as the 10-gene classifier), or a combination thereof, wherein the expression pattern of one or a combination of these genes, or proteins encoded thereby, is indicative of head and neck squamous cell carcinoma and lung squamous cell carcinoma. In particular embodiments, distinction is made between a primary lung squamous cell carcinoma and a metastatic head and neck squamous cell carcinoma of the lung. As used in the context of the present invention, the pattern of expression for one or a combination of the genes of the 10-gene classifier is obtained from a known population of samples with a HNSCC and LSCC. In particular embodiments, at least 1, 2, 3, 4, 5, 6, 7, 8, 9 or 10 of the genes of the 10-gene classifier are employed in generating the reference profile. As compared to a normal control profile, increased expression of CXCL13, COL6A2, KRT14, TMP3, KLK10, MMP1, GAS1, or MYH2 is indicative of HNSCC, in particular metastatic HNSCC, whereas increased expression of SFTPB or TSPYL5 is indicative of LSCC, in particular primary LSCC. Accordingly, in another embodiment, at least one gene or protein indicative of metastatic HNSCC and one gene or protein indicative of primary LSCC is employed in generating the reference profile.

The reference profile of the present invention finds application in a method of distinguishing between head and neck squamous cell carcinoma and lung squamous cell carcinoma in a patient. In particular embodiments, the reference profile is useful for distinguishing between primary squamous cell carcinoma of the lung and metastatic head & neck squamous cell carcinoma of the lung in patients with a previous history of HNSCC, as this determination is problematic and requires different treatments. As used in the context of the present invention, a patient or subject is intended to include a mammalian animal such as a human, a veterinary or farm animal, a domestic animal or pet, and animals normally used for clinical research. For diagnostic applications, a sample is any biological fluid (e.g., bronchoalveolar lavage fluid or sputum) or tissue that contains head, neck or lung cells indicative of or suspected of being cancerous.

In the diagnostic method of the invention, the expression level of CXCL13, COL6A2, SFTPB, KRT14, TSPYL5, TMP3, KLK10, MMP1, GAS1, or MYH2, or a combination thereof, is determined in a sample from a patient having or at risk of having a head and neck squamous cell carcinoma or lung squamous cell carcinoma to generate a test profile. The test profile is compared to the instant reference profile or a normal control profile (i.e., a healthy, disease-free sample) to determine whether the patient suffers from or is at risk of developing a head and neck squamous cell carcinoma or lung squamous cell carcinoma. For example, a patient sample with increased expression levels of SFTPB or TSPYL5 as compared to a normal control profile is indicative of LSCC, in particular primary LSCC. Similarly, a patient sample with increased expression levels of CXCL13, COL6A2, KRT14, TMP3, KLK10, MMP1, GAS1, or MYH2 as compared to a normal control profile is indicative of HNSCC, in particular metastatic HNSCC of the lung. Alternatively, a patient sample with comparable expression levels of SFTPB or TSPYL5 as compared to the instant reference profile is indicative of LSCC, e.g., primary LSCC. Likewise, a patient sample with comparable expression levels of CXCL13, COL6A2, KRT14, TMP3, KLK10, MMP1, GAS1, or MYH2 as compared to the instant reference profile is indicative of HNSCC, e.g., metastatic HNSCC. The comparison can be qualitative or quantitative, e.g., using a detection algorithm (as exemplified herein) to compare the 10-gene classifier expression profile of the patient sample with that of the average normal control/reference profiles previously established and returns a mathematical value or score reflecting which population the patient most closely resembles. In this regard, the instant diagnostic method is a platform-independent, discriminant method. Instead of using the calculated gene expression values, which can be different for different methods and might vary from one clinical setting to another, the relative ranks of gene expression are used. By using the ranks of gene expression, the analysis is remarkably robust. It is also method independent, in the sense that genes selected by microarrays of amplified RNA can be used to diagnose by PCR using total RNA. The discriminant function itself is transferable from one method to another, if a calibration standard is employed.

For DNA-based diagnostics, nucleic acid probes or primers can be readily generated by the skilled artisan based upon the disclosed UniGene identifiers of Table 2 so that the nucleic acid probes or primers bind to the nucleic acid sequences encoding the 10-gene classifiers of the invention. Such antisense sequences, as used herein, are intended to encompass single-stranded, partially single-stranded or double-stranded molecules that are sufficiently complementary to the nucleic acid sequence encoding the 10-gene classifiers, to be specifically hybridizable thereto. Such probes or primers may hybridize completely to the target sequences, i.e., 100% complementary. Alternatively, the probes or primers may hybridize with less than 100% avidity, but sufficiently to identify the target sequences from non-target sequences. Alternatively, such probes or primers may hybridize over one or more segments such that intervening or adjacent segments of the antisense sequence are not involved in the hybridization event (e.g., a loop structure or hairpin structure, such as a ribozyme).

Specifically contemplated by the present invention are chip-based DNA technologies for determining expression patterns of one or more of the 10-gene classifiers. Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see, e.g., Pease, et al. (1994) *Proc. Natl. Acad. Sci. USA* 91(11):5022-6; Fodor, et al. (1991) *Science* 251 (4995):767-73).

Various RT-PCR methodologies can also be employed to determine the level of RNA transcript of the 10-gene classifiers present in a sample. For conventional quantitative reverse-transcriptase polymerase chain reaction (QRT-PCR) assays, PCR products are sampled in the linear portion of their amplification curves. The number of PCR cycles that are optimal for sampling must be empirically determined for each target cDNA fragment. In addition, the reverse transcriptase products of each RNA population isolated from the various samples should be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to relative quantitative RT-PCR assays.

In addition to using microarray and quantitative RT-PCR analysis, immunoassays such as ELISA or immunohistochemical analysis of tissue arrays can be employed in carrying out the diagnostic method of the present invention. One advantage of immunohistochemical analysis is that it can be used in combination with paraffin-embedded tissues, which are most commonly used for standard clinical pathology (Ramaswamy (2004) *N. Engl. J. Med.* 350:1814-6). In general, the detection of proteins via immunoassays employs antibodies which specifically bind to proteins encoded by the nucleic acids of the 10-gene classifier. Antibodies which specifically bind these proteins can be either polyclonal or monoclonal. Moreover, such antibodies can be natural or partially or wholly synthetically produced. All fragments or derivatives thereof which maintain the ability to specifically bind the proteins are also included. The antibodies can be a member of any immunoglobulin class, including any of the human classes: IgG, IgM, IgA, IgD, and IgE. Antibodies to the disclosed proteins can be prepared using any conventional method (see, e.g., Kohler and Milstein (1975) *Nature* 256: 495-497; Harlow and Lane (1988) Antibodies: A Laboratory Manual, Cold Spring Harbor Laboratory, New York) and used in conventional immunoassays to detect the level of one or more proteins encoded by the nucleic acids of the 10-gene classifier.

The nucleic acid primers or probes and antibodies of the invention are desirably associated with, or conjugated to, a detectable label. The label on the reagent may be selected from the many known diagnostic labels, such as radioactive compounds, fluorescent compounds and proteins, calorimetric enzymes, etc. In one embodiment, the label can be a calorimetric enzyme, which upon contact with a substrate produces a detectable color signal. As another example, fluorochromes are commonly used labels for diagnostic reagents.

Commonly used fluorochromes include fluorescein isothiocyanate (FITC), phycoerythrin (PE), allophycocyanin (APC), and also include the tandem dyes, PE-cyanin-5 (PC5), PE-cyanin-7 (PC7), PE-cyanin-5.5, PE-Texas Red (ECD), rhodamine, PerCP, fluorescein isothiocyanate (FITC) and ALEXA® dyes. Any fluorochrome can be employed, including those excitable by radiation in the red, blue or green wavelengths or combinations thereof. All of these fluorescent dyes are commercially available, and their uses known to the art.

Methods for coupling or associating the label with diagnostic reagents are similarly conventional and known to those of skill in the art. Known methods of label attachment are described (see, for example, Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, Ill., 1994/1995). Thus, selection of the fluorochrome label(s) and coupling methods do not limit this invention.

Diagnostic reagents of this invention are usefully assembled into kits, which also contains miscellaneous reagents and apparatus for reading labels, e.g., certain substrates that interact with an enzymatic label to produce a color signal, etc., apparatus for taking samples, coated solid supports, miscellaneous substrates and apparatus for evoking or detecting the signals provided by the labels, as well as appropriate vials and other diagnostic assay components, and suitable packaging. Thus an embodiment of this invention is a diagnostic kit for use in distinguishing between head and neck squamous cell carcinoma and lung squamous cell carcinoma, which contains a diagnostic reagent of the invention, as well as other conventional diagnostic kit components. One of skill in the art may also readily select other conventional diagnostic components for this kit. Such kits and reagents may be employed in a method for distinguishing between head and neck squamous cell carcinoma and lung squamous cell carcinoma.

It is further contemplated that one or more genes of the 10-gene classifier disclosed herein can be used for identifying or monitoring the effects of a therapeutic agent or regimen on a patient having a head and neck squamous cell carcinoma or lung squamous cell carcinoma. According to such a method, a selected therapeutic agent or treatment regimen is administered to the patient. Periodically during and/or after administration of the agent or during and/or after completion of the therapeutic regimen, a sample containing cancerous head, neck or lung cells of the subject is examined for expression of one or more of the genes of the 10-gene classifier in the cells and based upon the expression levels of said gene(s), the effects of the therapeutic agent or regimen are evaluated.

The ongoing refinements in surgical therapy and in adjuvant chemotherapy for head and neck cancer and lung cancer make the distinction between primary LSCC and lung metastasis increasingly important. Thus, use of the method of the invention permits early diagnosis and treatment of LSCC and HNSCC by monitoring expression patterns of a small number of genes or proteins by analysis of patient samples in a clinical setting.

The invention is described in greater detail by the following non-limiting examples.

EXAMPLE 1

Patient Characteristics and Tissue Acquisition

Primary LSCC tumors were obtained from a tissue bank at the Thoracic Oncology Research Laboratory at the University of Pennsylvania. Lung cancer patients in this study presented to the Hospital of the University of Pennsylvania over a seven-year period and underwent a lobectomy for resection of LSCC. Clinical data was acquired via retrospective chart review. These patients had a confirmed pathological diagnosis of squamous cell carcinoma and had not received prior therapy. HNSCC patients in this study were obtained from a Head and Neck Carcinoma Tissue Bank and underwent surgical resection at over a four-year period (O'Donnell, et al. (2005) *Oncogene* 24:1244-51).

Intraoperative tumor samples were routinely dissected from surrounding normal tissue, but no micro-dissection was performed. Hematoxylin and eosin (H+E) staining was performed to verify the presence of greater than 70% tumor cells. Samples were immediately frozen in liquid nitrogen prior to RNA analysis.

EXAMPLE 2

RNA Preparation, Target Preparation, and Hybridization

RNA was extracted from the tumor specimens according to established methods (Singhal, et al. (2003) *Clin. Cancer Res.* 9:3080-97). All hybridization protocols were conducted as described in the AFFYMETRIX® GENECHIP® Expression Analysis Technical Manual. RNA was hybridized to AFFYMETRIX® U133A GENECHIP® (AFFYMETRIX®, Santa Clara, Calif.) using standard conditions in an AFFYMETRIX® fluidics station.

EXAMPLE 3

External Data Sources

Gene expression profiling data of HNSCC and LSCC tumor samples were provided by four external institutions. The samples were analyzed on two different AFFYMETRIX® chips U133A and U95Av2. U133A data included 41 HNSCC samples from the University of Minnesota (Ginos, et al. (2004) supra) U95Av2 data sets included 11 LSCC samples from Columbia University (Borczuk, et al. (2003) supra; Borczuk, et al. (2004) *Am. J. Respir. Crit. Care Med.* 170:167-7), 21 LSCC samples from the Dana-Farber Cancer Institute (Bhattacharjee, et al. (2001) *Proc. Natl. Acad. Sci. USA* 98:13790-5), and 49 samples (18 LSCC, 31 HNSCC) from Memorial-Sloan Kettering Cancer Center (Talbot, et al. (2005) supra). U95Av2 data from 12 squamous cell lung lesions from patients with previous HNSCC were also provided by the Memorial-Sloan Kettering Cancer Center (Talbot, et al. (2005) supra). The Dana-Farber Cancer Institute data was available from a public database. Patient characteristics and details of data acquisition, RNA isolation, and array hybridization have been described in the art for the four datasets.

EXAMPLE 4

Identifying U95Av2 and U133A Common Genes

Common genes were linked between the two chip types using AFFYMETRIX® probe set identifiers. Probe sets that were common between the two different platforms (U95Av2 versus U133A) were aligned using the "best match" file available from AFFYMETRIX®. This spreadsheet identifies the probe sets from the two platforms that are most similar based on several factors, including target sequence match and percent identity. A total of 9530 probe sets overlapped between U95Av2 and U133A.

EXAMPLE 5

Microarray Normalization

The CEL files for each dataset were reprocessed using a publicly available implementation of Robust Multichip Average expression summary (RMAExpress) v0.3 (Bolstad, et al. (2003) *Bioinformatics* 19:185-93). Default settings were used for background adjustment, quantile normalization, and Log2-transformation. Samples from the different institutions were processed as independent groups.

EXAMPLE 6

Distance Weighted Discrimination

The Distance Weighted Discrimination (DWD) method is a generalization of the Support Vector Machine (SVM), a multivariate technique (Vapnik & Chapelle (2000) *Neural Comput.* 12:2013-36). DWD has been previously shown to be well-suited for correction of the systematic biases in the context of microarray data (Benito, et al. (2004) supra) Its performance and robust quantification of systematic bias has been reported to be superior to that of classical methods (such as PCA, LDA, and standard linear SVM). This made DWD a method of choice for the adjustment of the different data sets presented herein. The detailed description of the method is known (see, Marron & Todd (2002) Distance Weighted Discrimination Technical Report No. 1339. School of Operations Research and Industrial Engineering, Cornell University). The DWD calculations were carried out using a Java-based version of DWD method publicly available from the University of North Carolina. The following settings were used for the input parameters: 1) DWD type—Non-Standardized DWD; 2) Mean Adjustment Type—Centered at the Second Mean.

EXAMPLE 7

Hierarchical Clustering

Hierarchical clustering was performed using the Pearson correlation distance metric and Ward's linkage. For visual enhancement, the clustering was carried out after the values for each gene were converted to z-scores by subtracting the corresponding gene mean that was computed over all samples being clustered, and dividing by the corresponding standard deviation.

EXAMPLE 8

Selection of Biomarkers

To identify genes that were differentially expressed between head & neck and lung squamous carcinomas, a univariate Student's two-tail heteroscedastic t-test was applied to the 18 head & neck and 10 lung samples processed at the University of Pennsylvania. In addition, selection of significant genes was carried out through Penalized Discriminant Analysis (PDA) (Raychaudhuri (2001) TIBS 19:189-93; Hastie, et al. (1995) *Annals Surgery* 23:73-102) trained on the same samples, by identification of the genes that contribute the most to the differences in discriminant scores between the two kinds of cancer. PDA is an extension of classic Fisher linear discriminant analysis (LDA) (Fisher (1938) *Annals Eugenics* 8:376-86) applied to the case when the number of covariates exceeds the number of observations in the training set. LDA would fail in this case, as it requires inversion of the covariance matrix, which would be singular. PDA deals with this problem by substituting the covariance matrix in the calculation of the discriminant weights by its sum with the identity matrix, which renders it non-singular.

EXAMPLE 9

PDA with Recursive Feature Elimination (RFE)

In this model-based (wrapper) approach, biologically important genes were identified as the genes that contributed the most to the classification model. These genes were selected as follows: at step 1, approximately 30% of the genes found to be the least differentially expressed between samples in positive (HNSCC) and negative (LSCC) sets were eliminated, based on the p-values from a univariate t-test performed on the 28 University of Pennsylvania samples constituting the training set. A progressive scheme of gene reduction begins with step 2: a discriminant model is then applied and the least informative genes (usually from 1 to 10%) are removed iteratively. This process is repeated until only one gene remains. A discriminant model is fitted at each reduction and each gene is assigned a computed "predictive power". The "predictive power" is discriminant weight×standard deviation, which estimates the contribution of that gene to the discriminant score. The discriminant scores (either positive or negative) define which of the 2 experimental classes a particular sample belongs and how well each sample is classified.

EXAMPLE 10

Resampling Procedure

To evaluate robustness of the instant classifier and to estimate the confidence intervals for the classification scores for each sample in the independent validation set; PDA with RFE was carried out on 100 subsets of the University of Pennsylvania training set and applied to classify the validation samples. The 100 training subsets were generated by random resampling without replacement (jackknifing) from 28 samples in the University of Pennsylvania dataset. Each subset contained 90% of the 28 original samples, with the same proportion of LCSS and HNSCC.

EXAMPLE 11

Quantitative Real-Time PCR

Gene-specific primer (IDT, Inc., Coralville, Iowa) were designed with Light Cycler Probe Design Software, Version 1.0 (Idaho Technology Inc., Salt Lake City, Utah) and ABI PRISM® PrimerExpress® software, Version 2.0 (Applied Biosystems® Inc., Foster City, Calif.). Primers were selected from the 3' half of the message using sequence retrieved from GenBank® database and in almost all cases from different exons. The PCR reaction was performed in 20 μL reactions according to established methods (Kari, et al. (2003) *J. Exp. Med.* 197:1477-88) using the Chromo4™ PTC-200® Peltier Thermal Cycler (MJ Research, Waltham, Mass.). All primers were designed to have a melting temperature of approximately 60° C. The PCR cycle parameters were: a 95° C. hot start for 3 minutes followed by 40 cycles of 95° C. for 20 seconds, 60° C. for 10 seconds, 72° C. for 20 seconds, and 78° C. for 5 seconds (to ensure elimination of side products). SYBR® Green I fluorescence intensity was measured at the end of each 72° C. extension according to known methods (Kari, et al. (2003) supra). Results were normalized to GAPDH as the housekeeping gene and values calculated relative to a standard cure generated using the Stratagene® universal standard RNA (Stratagene®, La Jolla, Calif.) which had been supplemented with RNA from the Jar and HT3 epithelial cell lines. The same standard RNA mixture was used for all comparisons. Product specificity was assessed by melting curve analysis and selected samples were run on 2% agarose gels for size assessment. Quality of real-time PCR was determined in two ways: the amplification efficiencies had to be 100%±10%, and correlation coefficients (r^2) greater than 95%. The cDNA for PCR amplification were prepared from 0.5 μg of the amplified RNA using Superscript™ II according to established methods. The amplified RNA was generated from 250 ng of total RNA subjected to one round of linear amplification using the RiboAmp® RNA Amplification Kit (Arcturus Inc., Mountain View, Calif.). Some samples were also assayed from cDNA prepared from total RNA with similar results.

EXAMPLE 12

Immunohistochemistry

Four formalin-fixed, paraffin-embedded LSCC tumors were sectioned to produce 4-μm sections which underwent immunohistochemical staining with a polyclonal antibody to proSP-C at a dilution of 1:2000 without antigen retrieval. This antibody was prepared using an SP-C$^{11-23}$ synthetic peptide as an immunogen (Beers, et al. (1994) *J. Biol. Chem.* 269: 20318-28). Immunohistochemical analysis was performed with the use of the standard avidin-biotin complex technique. Review of sections was performed by a skilled lung pathologist.

What is claimed is:

1. A kit for distinguishing between head and neck squamous cell carcinoma and lung squamous cell carcinoma comprising polynucleotides encoding the full lengths of CXCL13, COL6A2, SFTPB, KRT14, TSPYL5, TMP3, KLK10, MMP1, GAS1, and MYH2 selected as biomarkers for distinguishing between head and neck squamous cell carcinoma and lung squamous cell carcinoma.

2. The kit of claim 1, wherein the lung squamous cell carcinoma is a primary lung squamous cell carcinoma and the head and neck squamous cell carcinoma is metastatic.

3. A method for determining whether a tumor sample comprises head and neck squamous cell carcinoma or lung squamous cell carcinoma comprising determining polynucleotide expression levels for CXCL13, COL6A2, SFTPB, KRT14, TSPYL5, TMP3, KLK10, MMP1, GAS1, and MYH2 in a tumor sample from head and neck squamous cell carcinoma tissue or lung squamous cell tissue of a patient having head and neck squamous cell carcinoma or lung squamous cell carcinoma; and comparing said levels to control polynucleotide expression levels of CXCL13, COL6A2, SFTPB, KRT14, TSPYL5, TMP3, KLK10, MMP1, GAS1, and MYH2 in tumor tissue from head and neck squamous cell carcinoma tissue and to control polynucleotide expression levels of CXCL13, COL6A2, SFTPB, KRT14, TSPYL5, TMP3, KLK10, MMP1, GAS1, and MYH2 in tumor tissue from lung squamous cell carcinoma tissue, wherein, as compared to said controls, higher polynucleotide expression levels of CXCL13, COL6A2, KRT14, TMP3, KLK10, MMP1, GAS1, and MYH2 indicate that said tumor sample comprises head and neck squamous cell carcinoma and higher polynucleotide expression levels of SFTPB and TSPYL5 indicate that said tumor sample comprises lung squamous cell carcinoma.

4. The method of claim 3, wherein the lung squamous cell carcinoma is a primary lung squamous cell carcinoma and the head and neck squamous cell carcinoma is metastatic.

* * * * *